(12) United States Patent
Fisch et al.

(10) Patent No.: US 8,462,328 B2
(45) Date of Patent: Jun. 11, 2013

(54) EFFICIENT TELECENTRIC OPTICAL SYSTEM (ETOS)

(75) Inventors: David Fisch, D.N. Modi'im (IL); Yigal Katzir, Rishon Lezion (IL)

(73) Assignee: Orbotech Ltd., Yavne (IL)

( * ) Notice: Subject to any disclaimer, the term of this patent is extended or adjusted under 35 U.S.C. 154(b) by 217 days.

(21) Appl. No.: 13/003,725

(22) PCT Filed: Jul. 21, 2009

(86) PCT No.: PCT/IL2009/000714
§ 371 (c)(1),
(2), (4) Date: Jan. 11, 2011

(87) PCT Pub. No.: WO2010/010556
PCT Pub. Date: Jan. 28, 2010

(65) Prior Publication Data
US 2011/0122404 A1    May 26, 2011

Related U.S. Application Data

(60) Provisional application No. 61/129,822, filed on Jul. 22, 2008.

(51) Int. Cl.
*G01N 21/00* (2006.01)
(52) U.S. Cl.
USPC .................. 356/237.2; 356/237.1; 356/237.3; 356/394
(58) Field of Classification Search
USPC ............ 356/237.1–237.5, 392–394; 382/145, 382/141, 154; 250/559.43, 559.41, 559.45, 250/223 B
See application file for complete search history.

(56) References Cited

U.S. PATENT DOCUMENTS

| | | | |
|---|---|---|---|
| 4,030,830 | A | 6/1977 | Holly |
| 4,199,219 | A | 4/1980 | Suzki et al. |
| 4,465,371 | A | 8/1984 | Pernick |
| 4,592,625 | A | 6/1986 | Uehara |
| 4,629,319 | A | 12/1986 | Clarke et al. |
| 5,377,001 | A | 12/1994 | Malin et al. |
| 5,428,442 | A | 6/1995 | Lin et al. |
| 5,450,201 | A | 9/1995 | Katzir et al. |
| 5,497,234 | A | 3/1996 | Haga |
| 5,629,768 | A | 5/1997 | Hagiwara |

(Continued)

FOREIGN PATENT DOCUMENTS

| | | |
|---|---|---|
| JP | 07-198622 A | 8/1995 |
| JP | 2001-124661 A | 5/2001 |
| JP | 2002-250696 A | 9/2002 |
| JP | 2008-241469 A | 10/2008 |

*Primary Examiner* — Sang Nguyen
(74) *Attorney, Agent, or Firm* — Sughrue Mion, PLLC

(57) ABSTRACT

A new architecture for machine vision system that uses area sensor (or line sensor), with telecentric imaging optics compound with telecentric illumination module is described. The illumination module may include a bright field illumination source and/or a dark field illumination source. The telecentric imaging optics includes an upper imaging module having an aperture stop and a lower imaging module positioned between the upper imaging module and object, such that the light source and the aperture stop are located in the back focal plane of the lower imaging module. The lower imaging module images the illumination source into a plane of an aperture stop of the upper imaging module. The optical axis of the upper imaging module is offset with respect to the lower imaging module. The optical axis of the telecentric illumination module is offset with respect to the axis of the lower imaging module in the opposite direction.

25 Claims, 14 Drawing Sheets

U.S. PATENT DOCUMENTS

| | | |
|---|---|---|
| 5,715,050 A | 2/1998 | Haga |
| 5,737,074 A | 4/1998 | Haga et al. |
| 6,034,804 A | 3/2000 | Bashkansky |
| 6,122,046 A * | 9/2000 | Almogy ............ 356/237.2 |
| 6,198,529 B1 | 3/2001 | Clark, Jr. et al. |
| 6,222,624 B1 * | 4/2001 | Yonezawa ............ 356/237.1 |
| 6,496,254 B2 | 12/2002 | Bostrom et al. |
| 6,532,064 B1 * | 3/2003 | Hearn et al. ............ 356/237.1 |
| 6,603,874 B1 * | 8/2003 | Stern et al. ............ 382/144 |
| 6,633,375 B1 * | 10/2003 | Veith et al. ............ 356/237.4 |
| 6,870,949 B2 | 3/2005 | Baldwin |
| 6,980,249 B2 | 12/2005 | Albertelli |
| 7,072,034 B2 * | 7/2006 | Rosengaus et al. ........ 356/237.5 |
| 7,246,923 B2 * | 7/2007 | Conner ............ 362/309 |
| 7,271,889 B2 * | 9/2007 | Cemic et al. ............ 356/237.2 |
| 7,292,331 B2 | 11/2007 | Vertoprakhov |
| 7,295,303 B1 | 11/2007 | Vaez-Iravani et al. |
| 2003/0010930 A1 | 1/2003 | Thorwith et al. |
| 2003/0112428 A1 | 6/2003 | Oomori et al. |
| 2004/0207836 A1 * | 10/2004 | Chhibber et al. ......... 356/237.4 |
| 2005/0280808 A1 * | 12/2005 | Backhauss et al. ........ 356/237.2 |
| 2006/0209298 A1 | 9/2006 | Kvamme et al. |
| 2007/0009257 A1 | 1/2007 | Baldwin et al. |
| 2007/0147821 A1 | 6/2007 | Gaessler et al. |
| 2007/0222974 A1 | 9/2007 | Zhao et al. |
| 2008/0174771 A1 | 7/2008 | Yan et al. |

* cited by examiner

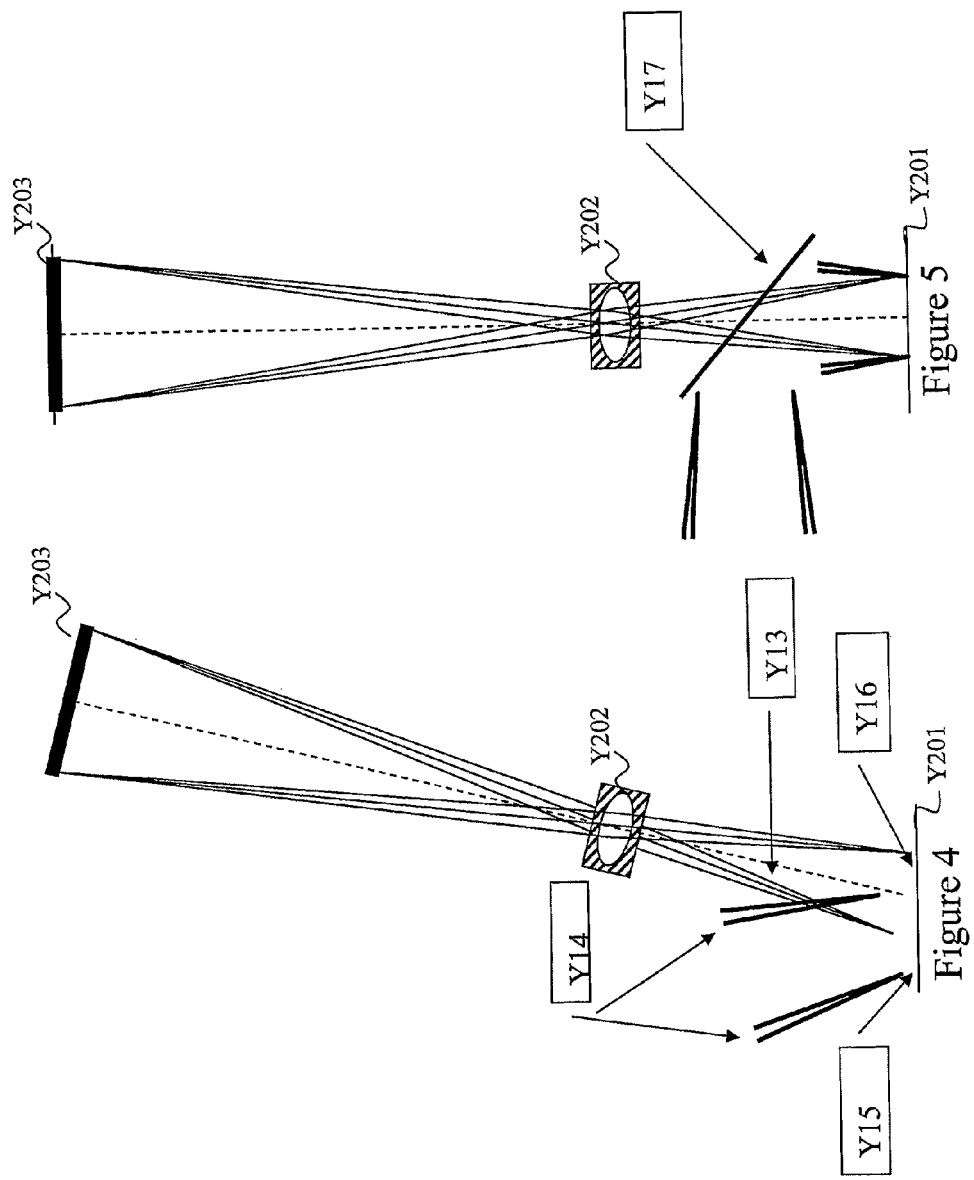

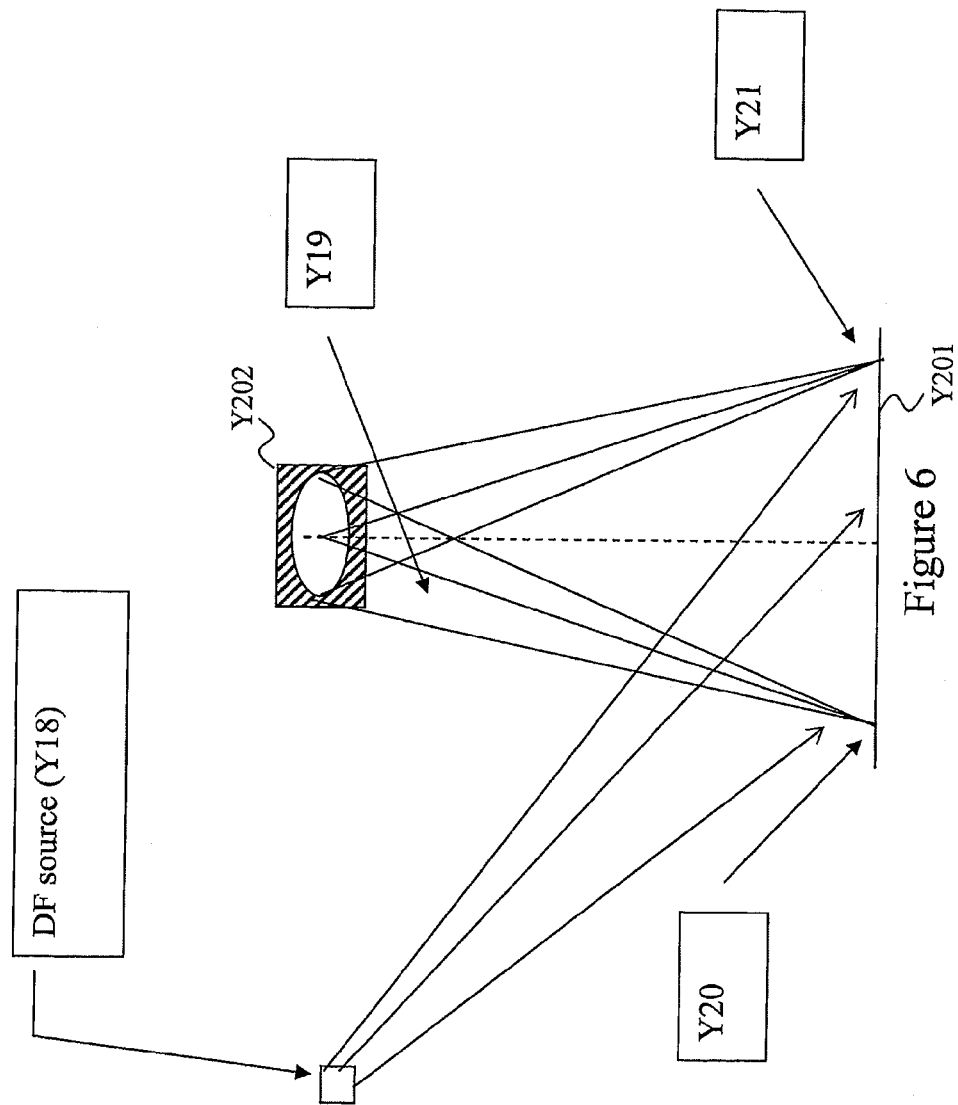

Illumination BF module as a sub system

EFFICIENT TELECENTRIC OPTICAL SYSTEM (ETOS)

CROSS-REFERENCE TO RELATED APPLICATION

This application is based on and claims the benefit of priority under 35 U.S.C. 119 from provisional U.S. patent application No. 61/129,822, filed on Jul. 22, 2008, the entire disclosure of which is incorporated by reference herein.

FIELD OF THE INVENTION

This invention generally relates to optical inspection systems and, more specifically, to designing of optical inspection systems having area imaging sensor (or line sensor) combined with telecentric imaging optics and telecentric object illumination.

DESCRIPTION OF BACKGROUND ART

During the production process of various electronic devices such as Flat Panel Displays (FPD) and Printed Circuit Boards (PCB), each device must be thoroughly inspected after various process steps in order to identify and possibly correct production defects and avoid incurring additional costs if the device cannot be repaired. For inspecting such devices, Machine Vision Inspection system Y100 shown in FIG. 1 can be used.

As shown in FIG. 1, a typical Machine Vision Inspection system Y100 for optically inspecting object Y102 uses illumination module Y101 to illuminate the object Y102. The image of the illuminated object Y102 is created using imaging optics Y103 at the location of the camera Y104. The camera Y104 converts the optical image of the object into digital representation, which is automatically processed by the data processing module Y105 in order to, for example, identify various production defects in the object. Two of the major design challenges associated with such inspection systems are:

1. Shaping the illumination light to fit the imaging requirements considering the interaction between the light and the object, which affect the image structure; and
2. How to make the illumination efficient in order to effectively utilize the necessary and available optical power.

As would be appreciated by those of skill in the art, in many situations, the angle of incidence of the illuminating light on the inspected object is very critical to how the image of the object is formed through the imaging optics of the inspection system. For example, while inspecting a reflective object, such as Flat Panel Display (FPD), which contains glass coated with thin film patterned layer, the major portion of the illuminating light reflected by the inspected object is specular (mirror like reflection of light). Creating the image of the object with the specularly reflected light is called Bright Field (BF) imaging.

Dark Field (DF) imaging, which is imaging in scattered light (which excludes the unscattered beam from the image), can also be implemented for inspection purposes. The Dark Field illumination/imaging is very efficient for purposes of inspection, however, the Dark Field illumination and imaging needs to be carefully specified, because it produces a different image type.

With reference to FIG. 2, in the case of non-telecentric imaging optics Y202, the Bright Field illumination beam (Y10) has to be shaped to match the collection angle beam (Y11) over the entire field, as shown in FIG. 2. When Bright Field image of the object is created using such optical configuration, overfilling illumination of the angles like (Y12), results in the light loss and, consequently, in lower performance of the inspection system, see FIG. 3. Thus, in order to ensure that sufficient light gets collected by the imaging sensor to produce an image of acceptable quality, the systems such as one shown in FIGS. 2 and 3 require higher power illuminating light source, which adds additional cost to the price of the system. Moreover, image quality parameters, such as resolution and contrast also suffer.

When the imaging is not telecentric, and the illumination device is a separate module from the imaging optics, it is often difficult to produce a good match between the Bright Field illumination light beam and the imaging optics. Two conventional methods that achieve matching the Bright Field illumination and the imaging are illustrated in FIGS. 4 and 5.

One such option, illustrated in FIG. 4, is tilting the optical axis of the imaging module (Y13), and the projection illumination beam (Y14) with respect to one another. This option has a disadvantage in that it results in defocus at the edges of the field of view (Y15) or (Y16) and makes it difficult to maintain optimal focus over the entire field of view, when it is larger than a thin line.

The second option, illustrated in FIG. 5, is to use a beam splitter (Y17) to direct the illumination light on the object. However, this approach is disadvantageous in that it has low optical power efficiency, and utilizes less than about 25% of the input optical power.

An exemplary implementation of the optical system for Dark Field imaging is shown in FIG. 6. It should be noted that images of inspected objects created using Dark Field imaging are very useful and informative for inspection purposes.

One method for providing Dark Field illumination on the object Y201, is locating the Dark Field illuminating light source (Y18) sufficiently outside the light collection angle area (Y19) of the imaging system. However, in a non-telecentric system, the point (Y20) in the field of view receives the Dark Field illuminating light at a different angle of incidence than the point (Y21) in the field of view. This results in dependence of the illuminating light incidence angle on the object on the position of the point within the field of view. This results, in turn, in change of appearance of the resulting Dark Field image across the field of view. Therefore, the Dark Field imaging requires uniformity in the illuminating light incidence angle across the field, which the system shown in FIG. 6 fails to provide. Illumination uniformity is especially critical in periodical structure inspection applications, where an image of one cell needs to be compared with an image of another. If the cells are differently illuminated, the aforesaid comparison of the respective images could be problematic.

Therefore, there is a need for systems and methods that achieve telecentric illumination and telecentric acquisition of the image of the inspected object in order to provide more uniform illumination, improved performance and better image quality parameters.

SUMMARY OF THE INVENTION

The inventive methodology is directed to methods and systems that substantially obviate one or more of the above and various other problems associated with conventional designs of optical inspection systems.

In accordance with one aspect of the inventive methodology, there is provided a system for optically inspecting an object. The inventive system incorporates a telecentric illumination system having an illumination optical axis and including a light source, the light source including a bright field illuminating light portion configured to illuminate the object with a bright field illuminating light. The inventive system further incorporates a telecentric optical imaging system including an imaging sensor and configured to create a bright field image of the object. In the inventive system, the telecentric optical imaging system further includes a first imaging module having a first optical axis and a second imaging module having a second optical axis. The aforesaid illumination optical axis, the first optical axis and the second optical axis are offset with respect to one another.

In accordance with another aspect of the inventive methodology, there is provided a system for optically inspecting an object. The inventive system incorporates a telecentric illumination system including a light source, the light source including a bright field illuminating light portion configured to illuminate the object with a bright field illuminating light and a dark field illuminating light portion configured to illuminate the object with a dark field illuminating light, the dark field illuminating light portion and the bright field illuminating light portion being disposed in the same plane. The inventive system further incorporates an optical imaging system including an imaging sensor and configured to create a bright field image of the object using a specular light reflected by the object and a dark field image of the object using a non-specular light.

In accordance with yet another aspect of the inventive methodology, there is provided a method for optically inspecting an object using a system incorporating a telecentric illumination system including a light source, the light source including a bright field illuminating light portion configured to illuminate the object with a bright field illuminating light and a dark field illuminating light portion including multiple segments, each of the multiple segments configured to illuminate the object with a dark field illuminating light having uniform angular distribution over an effective field of view, the dark field illuminating light portion and the bright field illuminating light portion being disposed in the same plane. The system further incorporates an optical imaging system including an imaging sensor and configured to create a dark field image of the object using a non-specular light. The inventive method involves selecting one of the multiple segments based on the features of the object; and creating a separate dark field image of the object, when the object is separately illuminated only by the selected one of the multiple segments to achieve a predetermined direction of incidence of the dark field illuminating light.

Additional aspects related to the invention will be set forth in part in the description which follows, and in part will be obvious from the description, or may be learned by practice of the invention. Aspects of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE FIGURES

The accompanying Figures, which are incorporated in and constitute a part of this specification exemplify the embodiments of the present invention and, together with the description, serve to explain and illustrate principles of the inventive technique. Specifically:

FIG. 4 illustrates a method for Bright Field illumination of the object using tilted optical axis.

FIG. 5 illustrates exemplary embodiment of the Bright Field illumination configuration using a beam splitter.

FIG. 6 illustrates Dark Field illumination configuration.

DETAILED DESCRIPTION OF PREFERRED EMBODIMENTS

In the following detailed description, reference will be made to the accompanying Figure(s), in which identical functional elements are designated with like numerals. The aforementioned accompanying Figures show by way of illustration, and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various elements may be made without departing from the scope and spirit of present invention. The following detailed description is, therefore, not to be construed in a limited sense. Additionally, the various embodiments of the invention as described herein may be implemented using a combination of generic optical components and/or specially developed optical modules.

Architecture

In accordance with an aspect of the inventive methodology, there is provided a novel architecture for machine vision system, which is illustrated with reference to FIG. 7. In one embodiment of the inventive technique, the system shown in FIG. 7 uses an area imaging sensor Y30, which can be a CCD sensor or a CMOS sensor. The aforesaid imaging sensor is optically coupled with telecentric imaging optics compound with telecentric illumination module.

Figure 1:
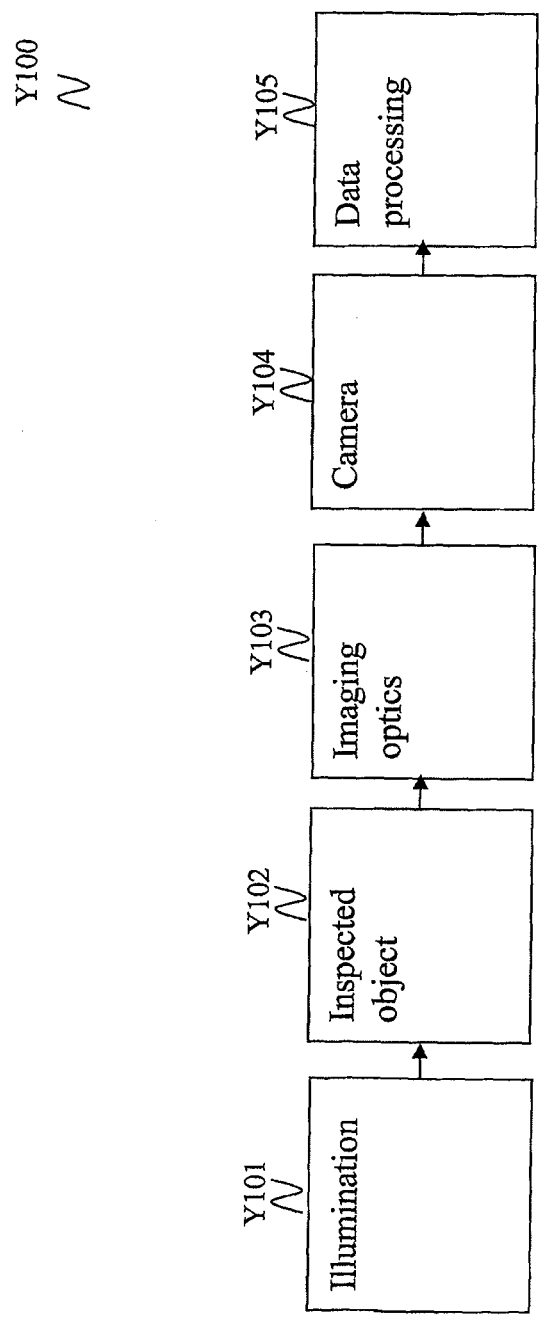
FIG. 1 illustrates a schematic block diagram of an exemplary machine vision inspection system.
Figure 3:
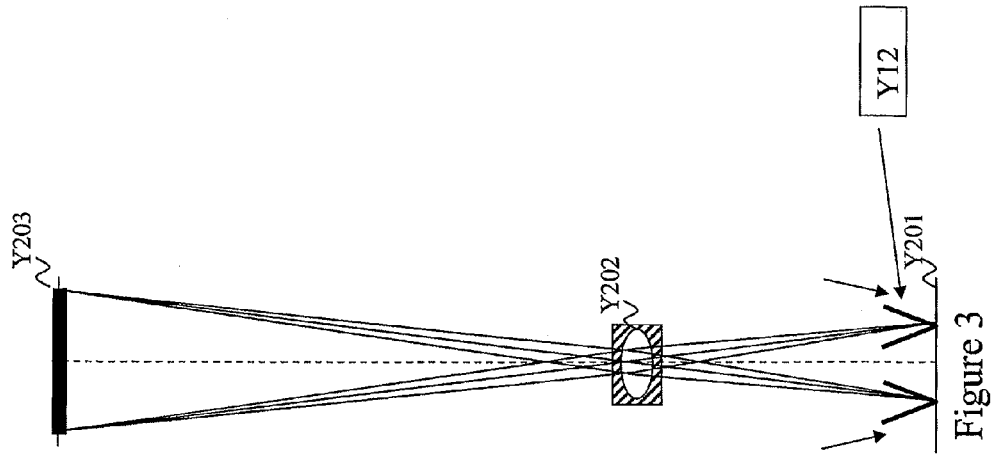
FIG. 3 illustrates exemplary illumination angle for Bright Field imaging.
Figure 2:
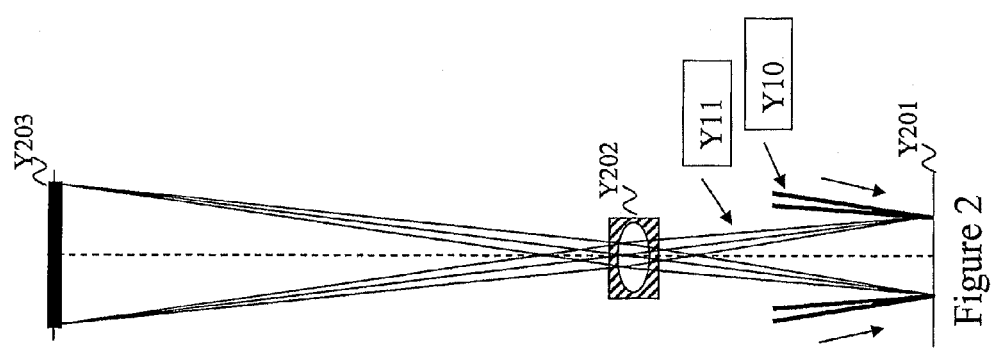
FIG. 2 illustrates exemplary illumination angle for Bright Field imaging.
Figure 7:
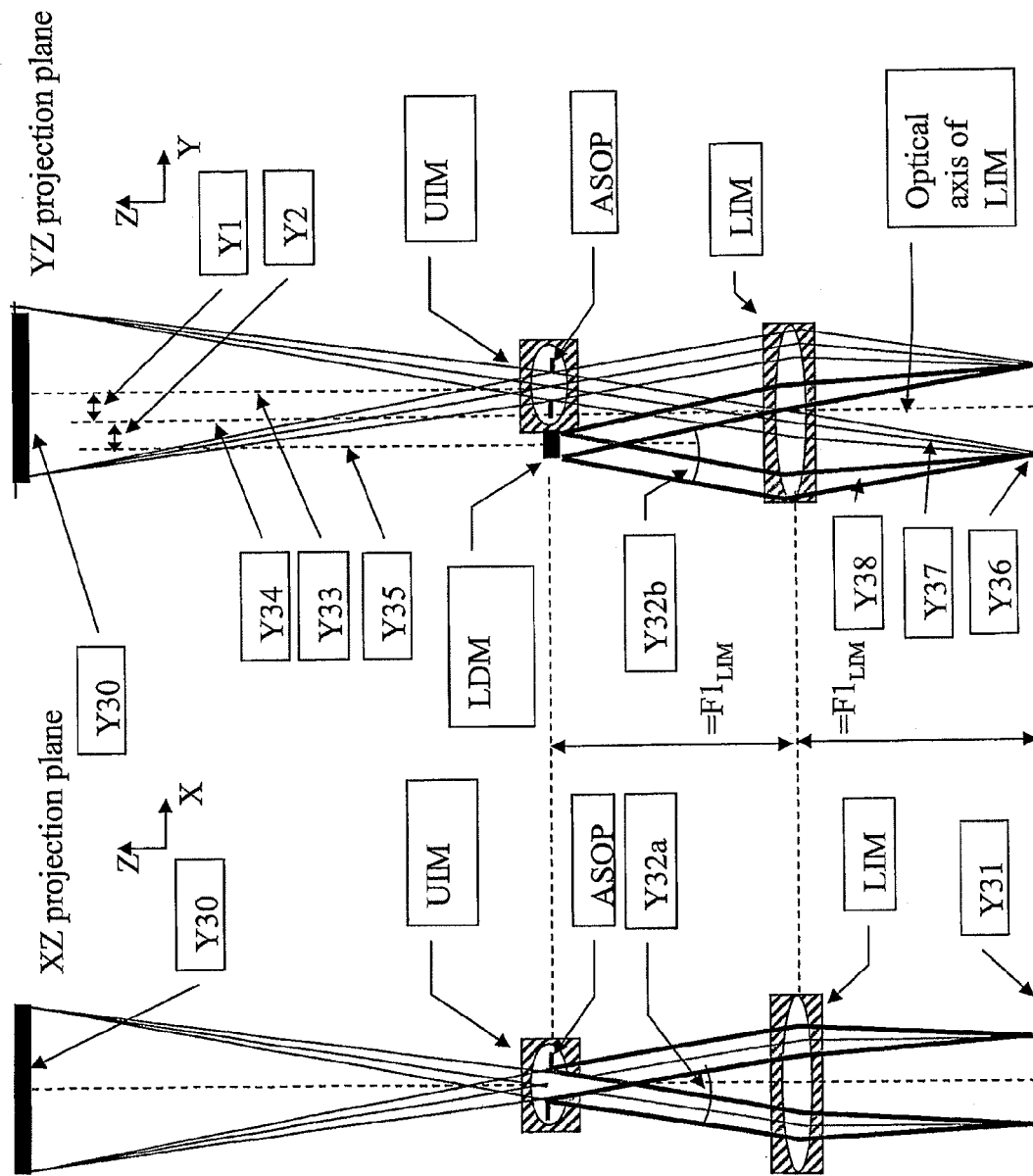
FIG. 7 illustrates an exemplary embodiment of the inventive telecentric illumination and imaging system.

In an embodiment of the invention shown in FIG. 7, the telecentric imaging optics is implemented as two separate sub modules, which may incorporate lenses and/or mirrors. It should be noted that other optical devices can also be incorporated into the aforesaid two sub-modules, consistent with the principles described herein. In an embodiment of the invention, there is provided a Lower Imaging Module (LIM) and an Upper Imaging Module (UIM). Both the LIM and UIM could be infinity corrected. Specifically, the LIM creates an image of the object, which is positioned in the object plane Y31, at infinity. The UIM re-images the aforesaid infinity located image to the plane of the imaging sensor Y30. Non infinity corrected embodiments are also advantageously possible as described herein below.

In the embodiment of the invention shown in FIG. 7, the aperture stop of the optical system (ASOP) is physically a part of the UIM. However, as would be appreciated by those of skill in the art, other implementations are possible. In an embodiment of the invention, for achieving the telecentric condition at the object plane Y31, the ASOP should preferably be located at the back focal plane of the LIM ($F1_{LIM}$).

In one embodiment of the invention, the optical system is configured to be telecentric also at the image plane. On the other hand, other implementations, which do not possess such a characteristic are also possible.

Illumination

In an embodiment of the invention, the light source (LDM) of the system, which delivers the illuminating light onto the object is implemented as an area having a disk shape. Preferably, the shape of the Bright Field light source of the system, which delivers the illumination light onto the object, has a shape that is matched to the shape of the ASOP. For example, if the ASOP is conveniently circularly shaped, the effective light source is preferably also circular or quasi-circular. A quasi-circular shape may be a square, hexagon or other similarly regular polygon. It should be noted however that the present invention is not limited to any disk-shaped light sources and other light source shapes could be used for illumination the object as well.

It should be noted that the light source LDM positioned as shown in FIG. 7 need not be a physical light source, but could be an image of the light source (referred to herein as logical light source) created using appropriate optical components, some of which will be discussed in detail below with reference to other figures.

The LDM emits illuminating light within certain angles, which are designated by legends Y32a and Y32b in FIG. 7. These angles are measured with respect to the axis Y35 of the LDM, which is perpendicular to its surface. In an embodiment of the invention, the LDM is located at the back focal plane of the LIM. The illumination light generated by the LDM passes through the LIM before impacting the object under inspection. Such positioning of the LDM ensures that the illumination provided by the LDM is telecentric at the object plane.

The system shown in FIG. 7 is characterized by a special feature—the UIM's optical axis Y33 is horizontally offset with respect to the LIM's optical axis Y34 by an amount Y1. The optical axis Y35 of the illuminator LDM is accordingly also horizontally offset with respect to the LIM's optical axis Y34 in the opposite direction by an amount Y2. In an embodiment of the invention, the value of Y1 is substantially equal to the value of Y2. In an embodiment of the invention the values of Y1 and Y2 are approximately equal to the linear dimension of the LDM.

One important characteristic of the exemplary embodiment of the optical configuration shown in FIG. 7 is that the effective light source, LDM is imaged into the ASOP plane through the LIM and the object plane acting as a mirror.

The embodiment of the novel optical system illustrated in FIG. 7 has the following desirable characteristics. First, the illumination provided by the LDM in the object plane 31 is telecentric, namely has nearly uniform angular distribution over the effective field of view. Second, the spatial distribution of the illuminating light across the field of view in the object plane is determined by the angular distribution of the light emitted by the light source LDM. Preferably, in an embodiment of the invention, LDM comprises LED light sources as described hereinbelow, which typically are characterized by quasi-Lambertian angular behavior. Such a configuration would result in the highest degree of uniformity of the illumination across the field of view. However, the present invention is not limited to only LED sources and other implementations of the LDM are possible.

As would be appreciated by those of skill in the art, a certain amount of optical vignetting (reduction of an image's brightness or saturation at the periphery compared to the image centre) can be tolerable in optical inspection systems. Specifically, it is known that non-uniformity of illumination of about 20% is acceptable for certain inspection applications.

As would be also appreciated by those of skill in the art, the embodiment of the inventive concept shown in FIG. 7 is characterized by the following advantage. Namely, because the LDM is imaged by the inventive optical system at the ASOP plane, by choosing the LDM shape and size such that it matches the geometry of the ASOP, the light beam Y38 reaching any point within the system's field of view, such as Y36, is reflected back by the specular object, see reflected light Y37, at the appropriate angle to fill the ASOP without undue overfilling if it is so desired. As the imaging system is preferably also telecentric, this relationship exists for all points over the entire field of view.

The aforesaid (almost) perfect matching between the projection beam angle Y38 and the collection beam angle Y37, is often desirable for achieving optimum imaging quality for inspection purposes. Moreover, the embodiment of the inventive system illustrated in FIG. 7 is advantageously efficient in terms of etendu conservation, because a major fraction of the light emitted by the LDM reaches the ASOP, and eventually the sensor Y30.

In practice, the relative positioning of the light source LDM, the LIM and the ASOP may deviate somewhat from the above preferable relationship, for example to mitigate system construction constraints. It will be appreciated by those of skill in the art that deviation of telecentricity by up to about 9 degrees is acceptable for most optical inspection applications.

Yet in addition, the embodiment of the system illustrated with reference to FIG. 7 is very efficient in term of radiance (brightness) conservation, due to the fact that the effective Bright Field illumination condition is achieved without the use of a beam splitter, unlike the conventional system shown in FIG. 5. Thereby, the inventive configuration avoids light losses associated with the use of the beam splitter.

Figure 8:
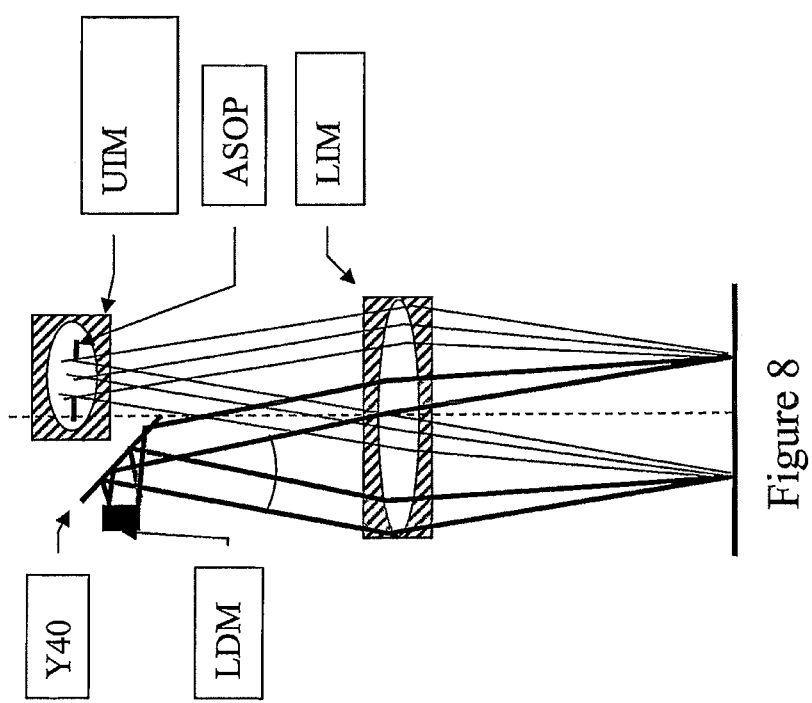
FIG. 8 illustrates an exemplary embodiment of the inventive telecentric illumination module.

It should be also noted that in an embodiment of the invention shown in FIG. 7, the ASOP and LDM are located very near to each other in the optical sense. Therefore, in another embodiment of the invention, illustrated in FIG. 8, a folding mirror Y40 is employed to allow more space for accommodating the light source LDM and its associated optics and mounting.

Selective Projection Angle

Figure 9:
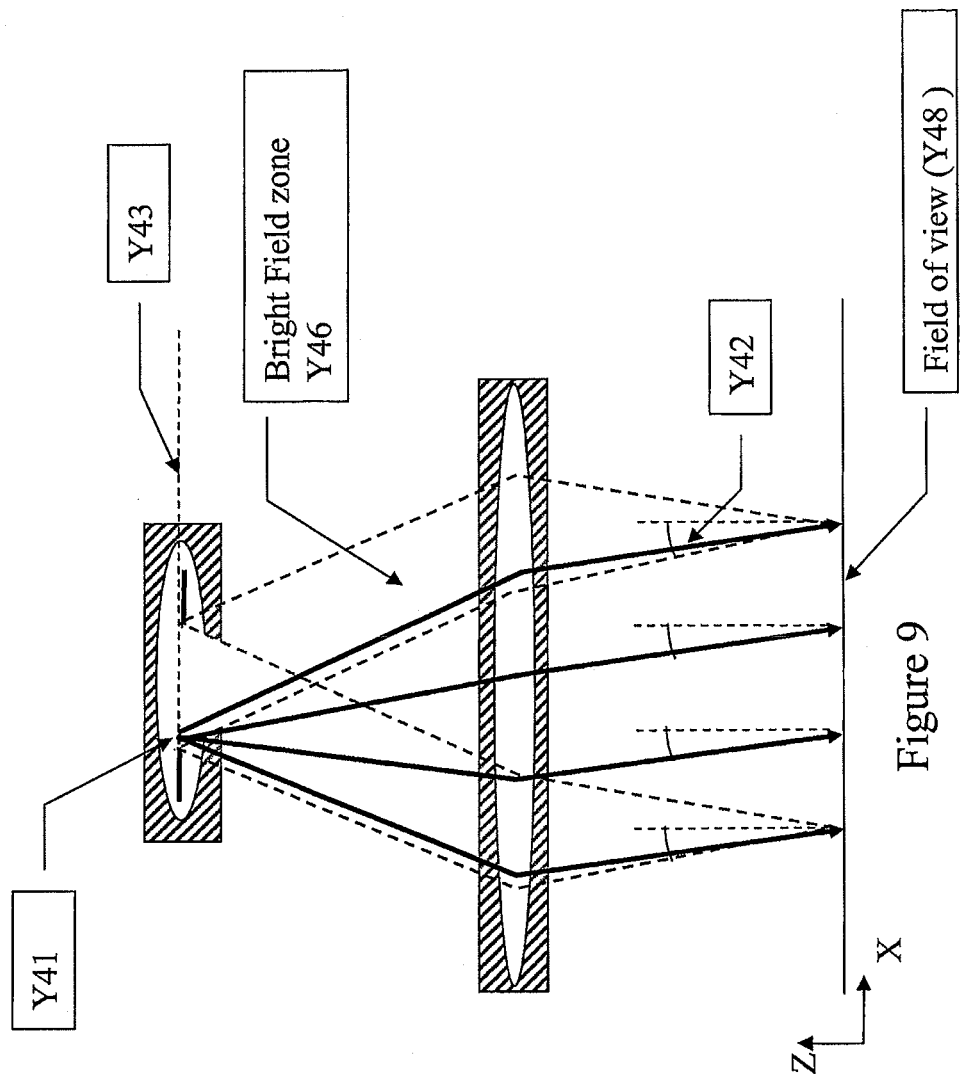
FIG. 9 illustrates a Bright Field angular zone in the illuminating pattern of the inventive illumination module.

In the foregoing telecentric imaging and illumination system described with reference to FIG. 7, each point in the LDM plane illuminates the entire field of view at the object plane, at a specific angle of incidence that is substantially similar for all points in the field. Referring now to the schematic illustration in FIG. 9, there is a direct conjugate relationship between any specific logical light emitting element such as Y41 in the LDM plane Y43, and an angle of incidence of the illuminating light Y42 in the object plane, which is substantially uniformly constant over the field of view Y48.

Figure 10:
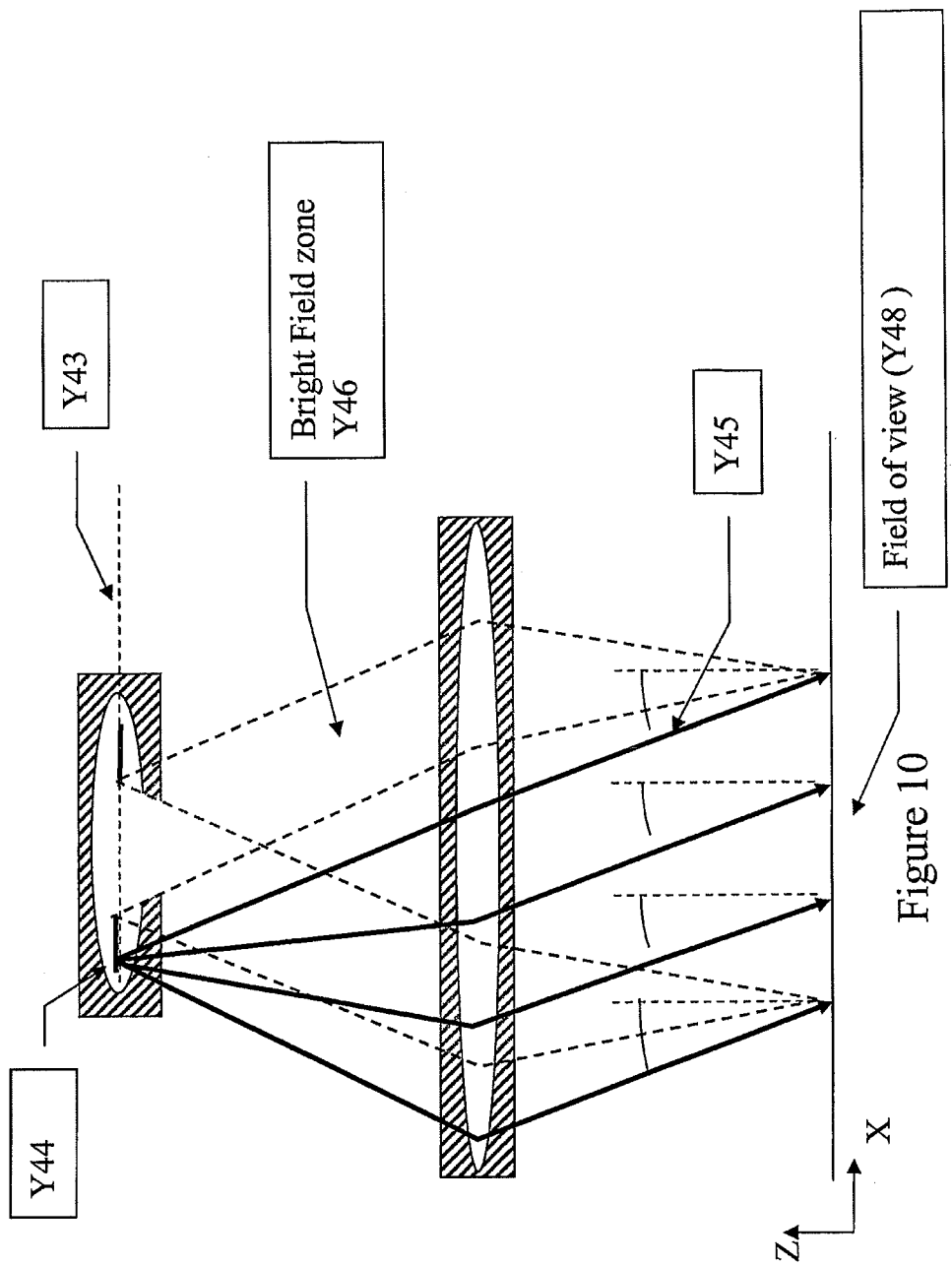
FIG. 10 illustrates Dark Field effective source point and exemplary light rays in the illuminating pattern of the inventive illumination module.

The above described conjugate relationship is not only valid for the Bright Field angular zone (designated by legend Y46 in FIGS. 9 and 10), but is also valid for the Dark Field angular zone lying outside the Bright Field zone. Exemplary Dark Field illumination light beams Y45 that are emitted by logical LDM light source point Y44 are illustrated in FIG. 10. Marginal Bright Field source points and light rays are superimposed with dashed lines for reference purposes. It should be noted that in an embodiment of the invention, the Dark Field illuminating light source is disposed in the same plane with the Bright Field illuminating light source (Fourier plane). As would be appreciated by persons of skill in the art, such configuration achieves telecentric Dark Field illumination.

Figure 11:
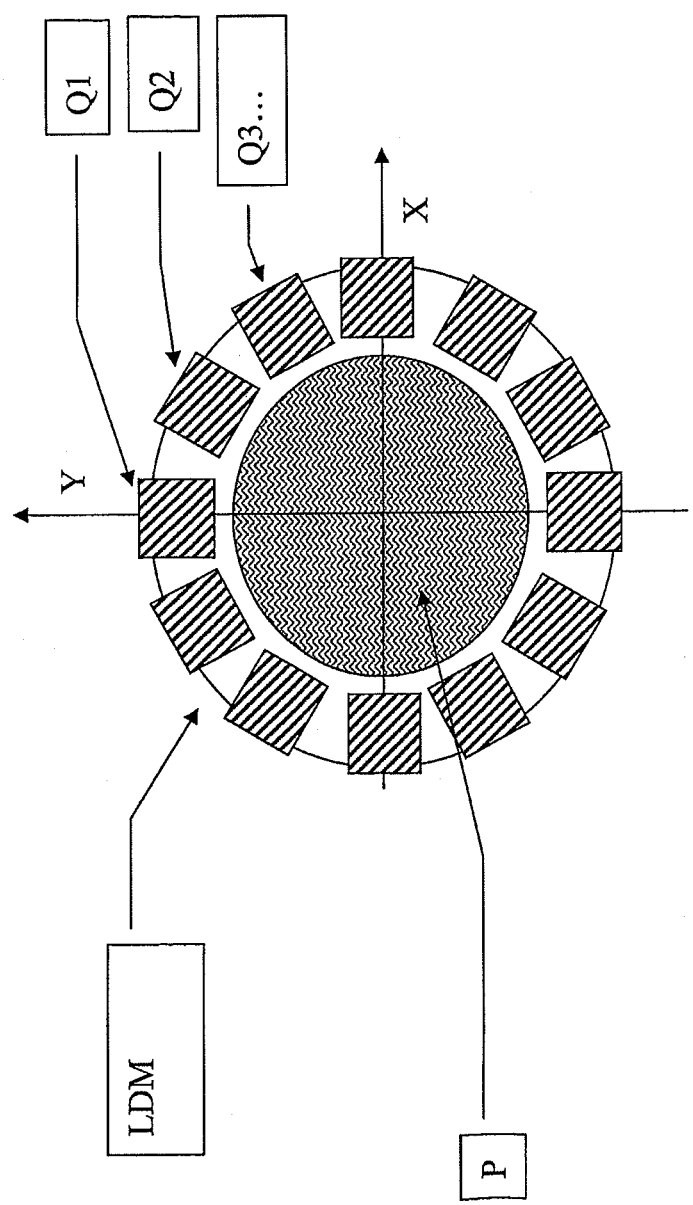
FIG. 11 illustrates an exemplary arrangement of the Bright Field and Dark Field illuminating light sources in the inventive illumination module.

To selectively control the angle of incidence of the illuminating light on the object, in an embodiment of the invention, the light source LDM incorporates separately controlled lighting segments, such as Dark Field generating segments Q1, Q2, Q3 . . . illustrated in FIG. 11. In the embodiment described in FIG. 11 the Dark Field generating segments are arranged in a ring surrounding the disk shaped Bright Field generating segment P. The light source configuration illustrated in FIG. 11 enables an embodiment of the inventive system to selectively project light on the object at selectively controlled angles, substantially uniformly over the object field of view. This can be used for creating a selectively controlled Dark Field illumination of the object.

Figure 12:
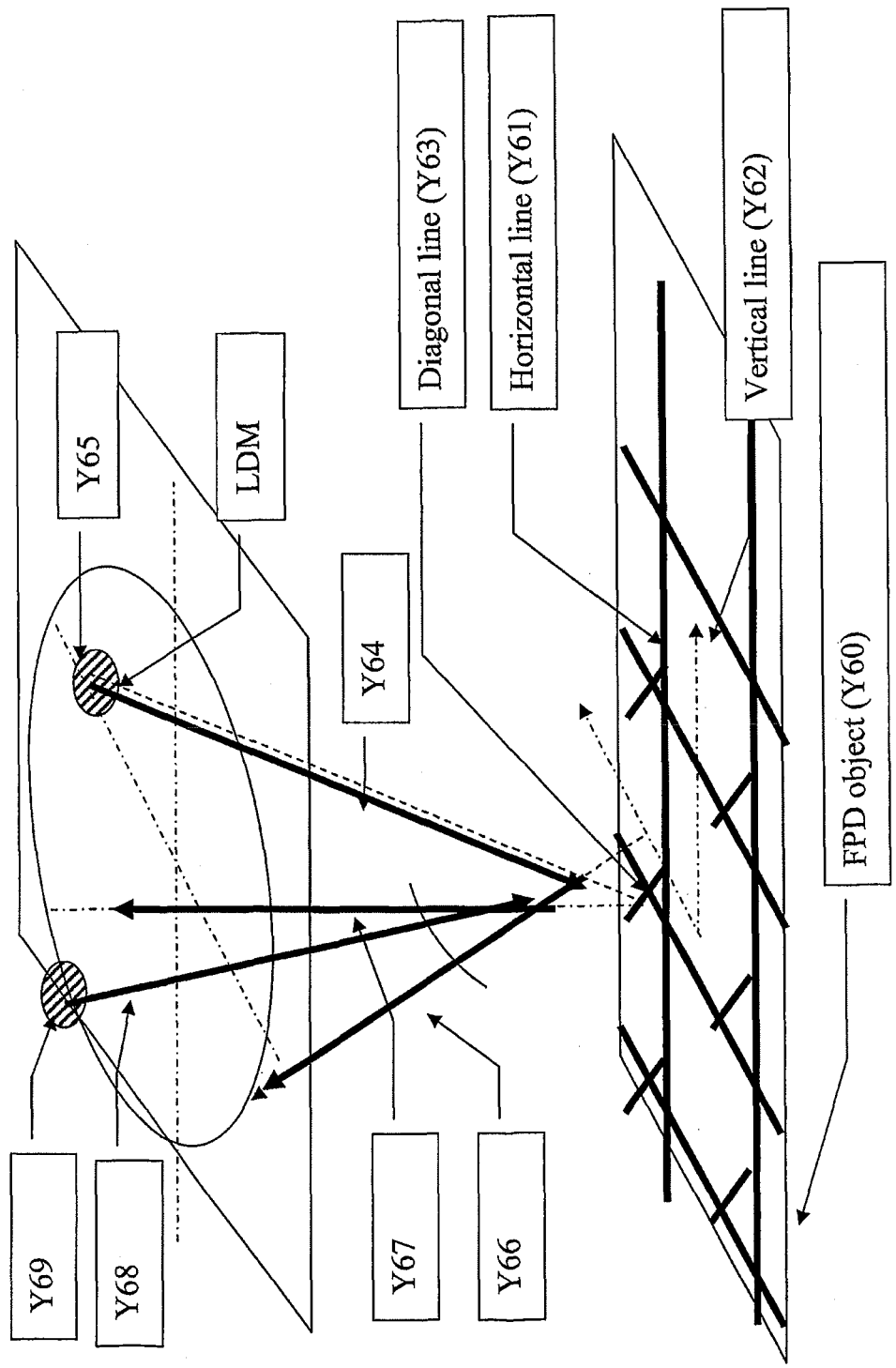
FIG. 12 illustrates Dark Field illumination of exemplary FPD pattern using light sources of the inventive illumination module.

For certain inspection tasks, for example in the manufacture of Flat Panel Displays (FPD), selective Dark Field is important for generating adequate image quality. Referring now to FIG. 12, a Flat Panel Display (FPD) panel usually contains a periodic structure, which is made up of horizontal lines Y61, vertical lines Y62 and diagonal lines Y63. FIG. 12 also shows two Dark Field light source segments Y65 and Y69 located in the LDM plane, suitably offset from the vertical direction at different azimuthal positions in the LDM plane.

With respect to the direction of the diagonal line Y63, the light source segment Y65 is offset substantially perpendicular in the azimuthal plane, whereas source segment Y69 is offset substantially parallel to the direction of the diagonal line Y63. Light ray Y64 which is emitted by the source segment Y65 is incident on pattern line Y63. Typically, most of the energy of the light ray Y64 is specularly reflected from the FPD planar surface as light ray Y66. Additionally, however, part of the energy of the light ray Y64 is diffracted by the edges of the line Y63. Light ray Y67 is one particular diffracted order emitted at normal direction to the FPD plane Y60. As will become apparent to those skilled in the art, the light ray Y64 will be diffracted more strongly in the direction perpendicular to the FPD surface by the edges of the line Y63 in comparison with another light ray, such as Y68 emitted by parallel offset source segment Y69.

The telecentric imaging system according to an embodiment of the present invention, such as illustrated with reference to FIG. 7, advantageously collects Dark Field diffracted light at a well defined Numerical Aperture (NA) around substantially parallel chief rays that are nearly perpendicular to the FPD plane at all points within the field of view. In a Dark Field illumination system implemented according to embodiments of the present invention, as depicted schematically in FIG. 10, all object points within the field of view are illuminated by substantially parallel light beams originating from a given light source location. When only a portion such as source segment Y65 of the Dark Field illumination light source is turned on, feature edges aligned substantially diagonally, such as line Y63 in FIG. 12 will appear brighter in the image generated by the sensor Y30 shown in FIG. 7, relative to other features whose edges are aligned in other directions.

The foregoing example demonstrates a particularly useful feature of the embodiments of the present invention, namely the ability to highlight specific object features by selectively controlling the direction (incidence angle on the object) of the Dark Field illumination. Such capability is often desired in the inspection of Flat Panel Displays (FPD).

Illumination Unit

Figure 13:
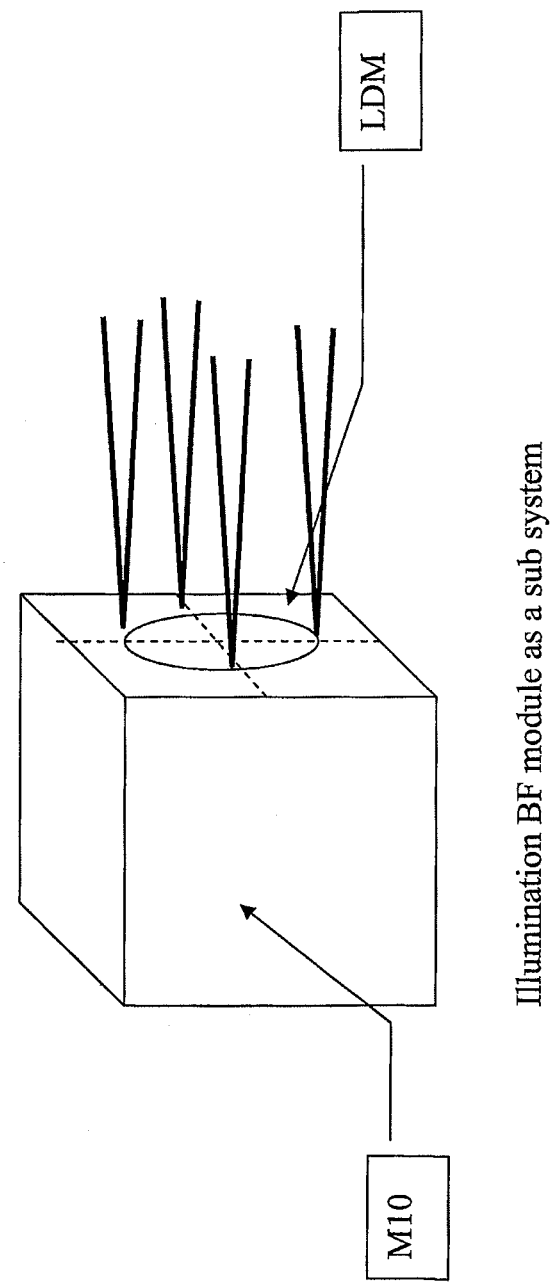
FIG. 13 illustrates an exemplary embodiment of the inventive Bright Field illumination module.

FIG. 13 illustrates one potential optical scheme for implementing light source module M10 having the light output with the required lighting characteristics of the LDM. In one embodiment of the invention, the light source module M10 is implemented using LEDs. However, as would be appreciated by those of skill in the art, the light source module M10 may be implemented using other light source types, including, without limitation, an arc lamp or a quartz halogen (QH) light source. Thus, the present invention is not limited to the disclosed light source types.

Figure 14:
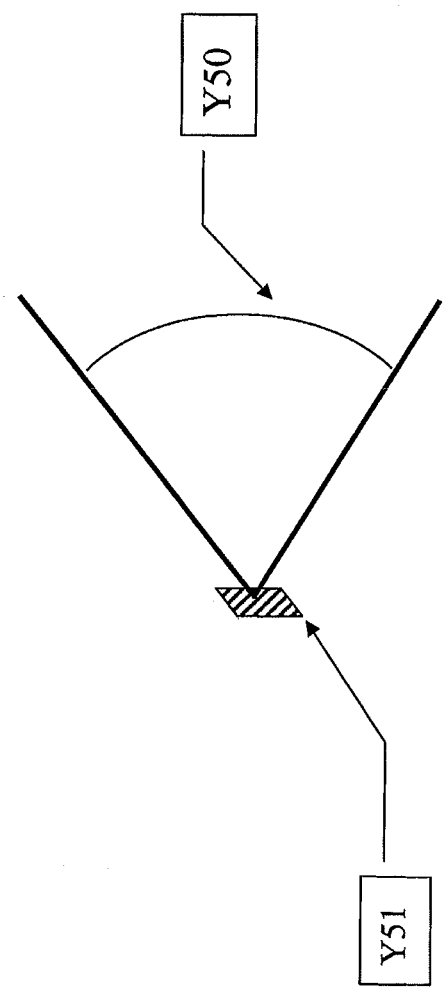
FIG. 14 illustrates an exemplary illumination pattern of an LED.
Figure 15:
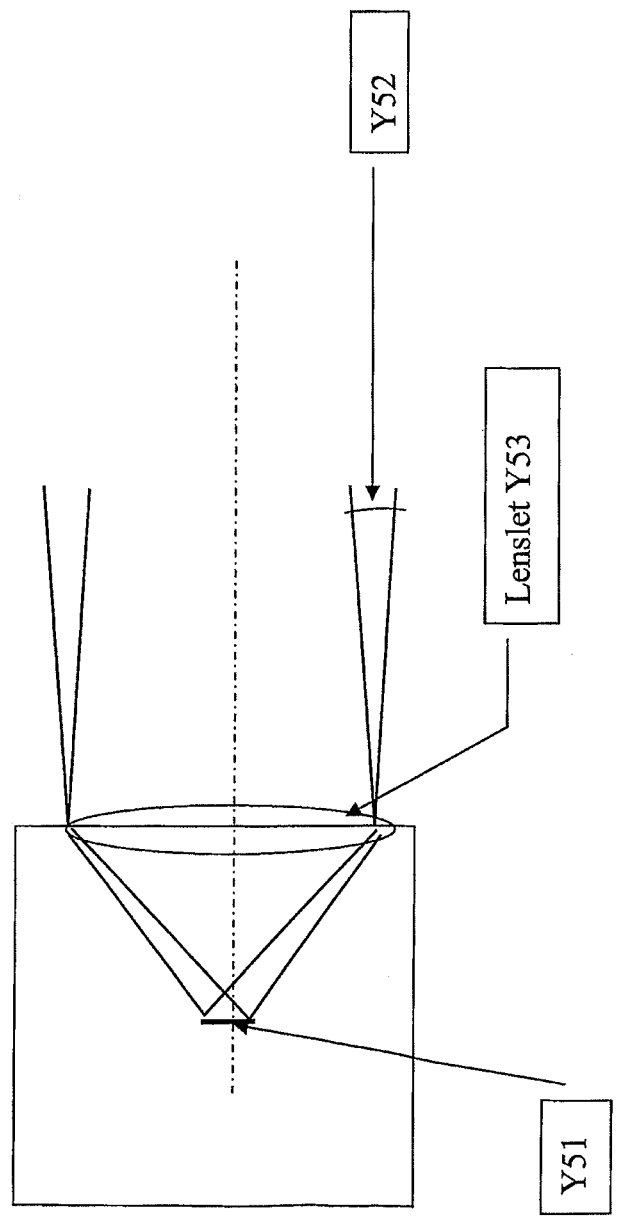
FIG. 15 illustrates an exemplary embodiment of the inventive illumination module and corresponding emitting angle.

FIG. 14 shows an LED die Y51 emitting light at a relatively wide angle Y50. In an embodiment of the invention, the LED die Y51 can be located at a focal plane of a lenslet Y53, as illustrated in FIG. 15. Now, the aperture of lenslet Y53 by itself may be considered a secondary effective light source having a larger diameter relative to LED die Y51, and a correspondingly narrower emitting angle Y52. As will be apparent to those skilled in the art, by suitably selecting the light source size and the lenslet optical parameters, it is possible to shape the output light for desired spatial and angular properties while conserving the original etendu and brightness. The configuration of FIG. 15 is an exemplary embodiment of the Bright Field segment of the LDM.

Figure 16:
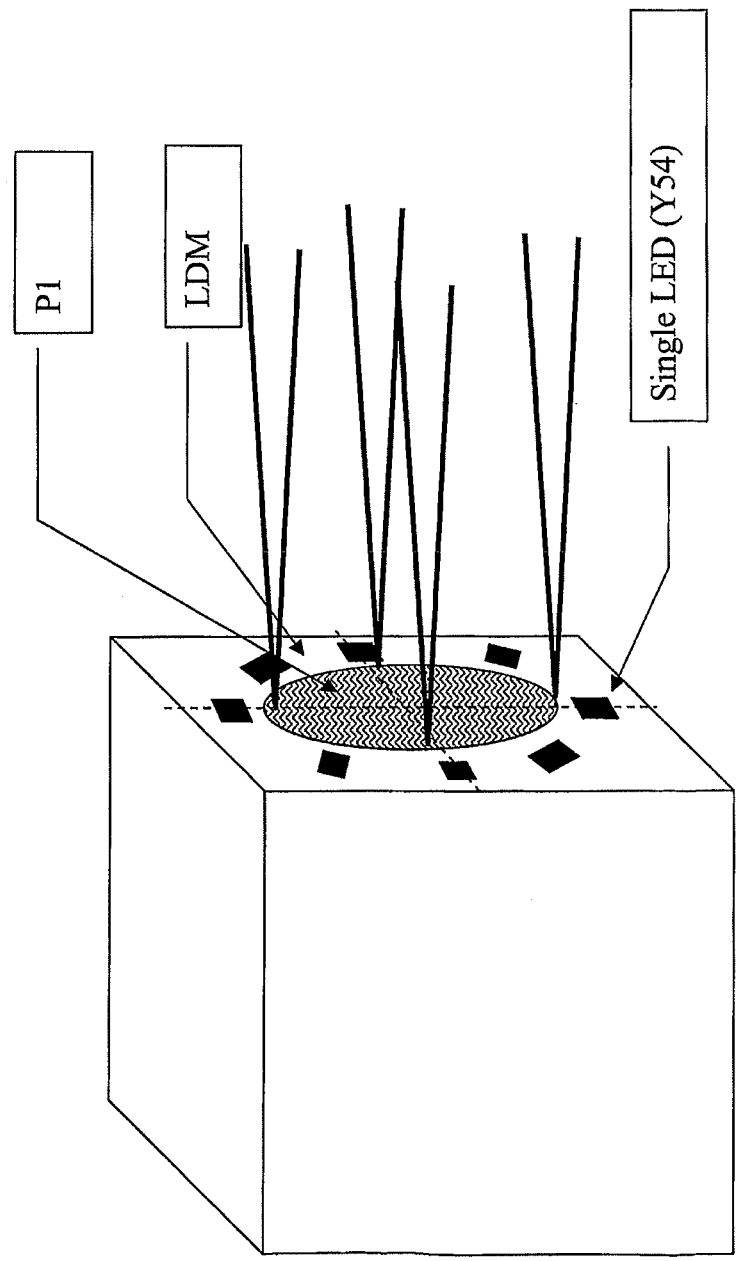
FIG. 16 illustrates another exemplary embodiment of the illumination module configured to enable selective Dark Field illumination of the object by separately controlled LEDs.

In an embodiment of the invention, for applications when a selective illumination of the object using relatively small segments of the illuminating light source LDM is required (e.g. for selective Dark Field imaging), the LDM is implemented by mounting separate LEDs such as LED Y54 in the LDM plane, as illustrated in FIG. 16. The LEDs are positioned in a ring surrounding the Bright Field illumination segment P1 in FIG. 16.

In an alternative embodiment of the invention, the LDM is implemented by placing or optically imaging a segmented spatial light modulator (SLM) such as a liquid crystal display (LCD) or a digital micromirror device (DMD) at the designated LDM plane. As will be appreciated by those skilled in the art, this embodiment provides additional flexibility with respect to defining the shape of the effective light source by selectively controlling each of the segments of the SLM using a computer control system. Furthermore, in such embodiment the shape of the effective light source can be changed at will under computer control to suit the application.

Magnification

In certain optical inspection tasks there is a need for variable magnification of the optical imaging system. One possible method to achieve variable magnification of the optical imaging system is to change the position of the entire module comprising UIM, LIM, ASOP, illumination as a whole relative to the object, and move the sensor accordingly to the newly defined image plane.

In one embodiment of the inventive concept, the variable magnification is achieved by properly designing either or both the optical parts designated as UIM and LIM in FIG. 7 to have a variable focal length while keeping the location of the aperture ASOP at the back focal plane of the LIM. Alternatively or additionally, either UIM or LIM could be designed to have variable principal plane locations.

Finally, it should be understood that processes and techniques described herein are not inherently related to any particular apparatus and may be implemented by any suitable combination of components. Further, various types of general purpose devices may be used in accordance with the teachings described herein. It may also prove advantageous to construct a specialized apparatus to perform the method steps described herein. The present invention has been described in relation to particular examples, which are intended in all respects to be illustrative rather than restrictive. Those skilled in the art will appreciate that many different combinations of hardware, software, and firmware will be suitable for practicing the present invention.

Moreover, other implementations of the invention will be apparent to those skilled in the art from consideration of the specification and practice of the invention disclosed herein. Various aspects and/or components of the described embodiments may be used singly or in any combination in the inventive telecentric optical inspection system. It is intended that the specification and examples be considered as exemplary only, with a true scope and spirit of the invention being indicated by the following claims and their equivalents.

What is claimed is:

1. A system for optically inspecting an object, the system comprising:
   a. a telecentric illumination system having an illumination optical axis and comprising a light source, the light source comprising a bright field illuminating light portion configured to illuminate the object with a bright field illuminating light; and
   b. a telecentric optical imaging system comprising an imaging sensor and configured to create a bright field image of the object, wherein the telecentric optical imaging system further comprises a lower imaging module having a first optical axis and an upper imaging module having a second optical axis and wherein the illumination optical axis, the first optical axis and the second optical axis are all parallel and are offset with respect to one another in a lateral direction, substantially perpendicular to the illumination optical axis, the first optical axis, and the second optical axis, and wherein light reflected by the object passes through both the lower imaging module and the upper imaging module prior to being incident on the imaging sensor.

2. The system of claim 1, wherein the imaging sensor comprises an area imaging sensor.

3. The system of claim 1, wherein the bright field illuminating light portion comprises at least one light emitting diode (LED).

4. The system of claim 3, wherein the telecentric illumination system further comprises a lenslet optically coupled with the LED.

5. The system of claim 1, wherein the light source further comprises a dark field illuminating light portion disposed in the same light source plane with the bright field illuminating light portion and configured to illuminate the object with a dark field illuminating light and wherein the telecentric optical imaging system is further configured to create a dark field image of the object.

6. The system of claim 5, wherein the dark field illuminating light portion comprises a plurality of dark field illuminating light segments, each of the plurality of dark field illuminating light segments configured to illuminate the object with the dark field illuminating light having uniform angular distribution over an effective field of view, wherein the each of the plurality of dark field illuminating light segments is separately controlled to achieve a predetermined direction of incidence of the dark field illuminating light.

7. The system of claim 6, wherein each of the dark field illuminating light segments comprises a light emitting diode.

8. The system of claim 6, wherein the bright field illuminating light portion has a circular shape and wherein the plurality of dark field illuminating light segments are arranged in a circle around the bright field illuminating light portion.

9. The system of claim 6, wherein for each selected one of the plurality of dark field illuminating light segments, the telecentric optical imaging system is configured to create a separate dark field image of the object, when the object is separately illuminated only by the each selected one of the plurality of dark field illuminating light segments and wherein the one of the plurality of dark field illuminating light segments is selected based on features of the object.

10. A system for optically inspecting an object, the system comprising:
    a. a telecentric illumination system having an illumination optical axis and comprising a light source, the light source comprising a bright field illuminating light portion configured to illuminate the object with a bright field illuminating light; and
    b. a telecentric optical imaging system comprising an imaging sensor and configured to create a bright field image of the object, wherein the telecentric optical imaging system further comprises a first imaging module having a first optical axis and a second imaging module having a second optical axis and wherein the illumination optical axis, the first optical axis and the second optical axis are offset with respect to one another,
    wherein the light source further comprises a dark field illuminating light portion disposed in the same light source plane with the bright field illuminating light portion and configured to illuminate the object with a dark field illuminating light and wherein the telecentric optical imaging system is further configured to create a dark field image of the object, and
    wherein the light source comprises a segmented spatial light modulator having a first plurality of segments forming the bright field illuminating light portion and a second plurality of segments forming the dark field illuminating light portion, wherein the first plurality of segments and the second plurality of segments are positioned or imaged in the light source plane.

11. The system of claim 10, wherein the segmented spatial light modulator comprises a liquid crystal display.

12. The system of claim 10, wherein the segmented spatial light modulator comprises a micromirror device.

13. The system of claim 10, further comprising a system for selectively controlling each of the first plurality of segments and each of the second plurality of segments to achieve a predetermined shape of the bright field illuminating light portion or the dark field illuminating light portion.

14. A system for optically inspecting an object, the system comprising:
    a. a telecentric illumination system having an illumination optical axis and comprising a light source, the light source comprising a bright field illuminating light portion configured to illuminate the object with a bright field illuminating light; and
    b. a telecentric optical imaging system comprising an imaging sensor and configured to create a bright field image of the object, wherein the telecentric optical imaging system further comprises a first imaging module having a first optical axis and a second imaging module having a second optical axis and wherein the illumination optical axis, the first optical axis and the second optical axis are offset with respect to one another, wherein the lower imaging module is positioned between the object and the upper imaging module and wherein the upper imaging module comprises an aperture stop located in a back focal plane of the lower imaging module.

15. The system of claim 14, wherein a size and a shape of the bright field illuminating light portion corresponds, respectively, to a size and a shape of the aperture stop.

16. The system of claim 14, wherein an image of the light source is located in a back focal plane of the lower imaging module and wherein the bright field illuminating light passes through the lower imaging module before illuminating the object.

17. The system of claim 14, wherein the second optical axis of the upper imaging module is offset with respect to the optical axis of the lower imaging module by a first offset value in a first direction and the illumination optical axis is offset with respect to the first optical axis of the lower imaging module in a second direction, opposite the first direction, by a second offset value.

18. The system of claim 17, wherein the first offset value is substantially equal to the second offset value.

19. The system of claim 17, further comprising a mirror, wherein light output from the light source is deflected by the mirror.

20. The system of claim 14, wherein the lower imaging module and the upper imaging module are both infinity-corrected.

21. The system of claim 14, wherein the light output by the light source is directed by the lower imaging module into the aperture stop.

22. The system of claim 14, wherein the upper imaging module is characterized by variable focal length and wherein the telecentric optical imaging system provides a variable magnification of the object.

23. A system for optically inspecting an object, the system comprising:
 a. a telecentric illumination system having an illumination optical axis and comprising a light source, the light source comprising a bright field illuminating light portion configured to illuminate the object with a bright field illuminating light and a dark field illuminating light portion configured to illuminate the object with a dark field illuminating light, the dark field illuminating light portion and the bright field illuminating light portion being disposed in the same light source plane; and
 b. an optical imaging system comprising an imaging sensor and configured to create a bright field image of the object and a dark field image of the object, wherein the optical imaging system is a telecentric optical imaging system further comprising a lower imaging module having a first optical axis and an upper imaging module having a second optical axis, wherein the illumination optical axis, the first optical axis, and the second optical axis are all parallel and are offset with respect to one another in a lateral direction, substantially perpendicular to the illumination optical axis, the first optical axis, and the second optical axis, and wherein light reflected by the object passes through both the lower imaging module and the upper imaging module prior to being incident on the imaging sensor.

24. The system of claim 23, wherein the dark field illuminating light portion comprises a plurality of dark field illuminating light segments, each of the plurality of dark field illuminating light segments configured to illuminate the object with the dark field illuminating light having uniform angular distribution over an effective field of view, wherein the each of the plurality of dark field illuminating light segments is separately controlled to achieve a predetermined direction of incidence of the dark field illuminating light.

25. A method for optically inspecting an object using a system comprising:
 a telecentric illumination system comprising a light source, the light source comprising a bright field illuminating light portion configured to illuminate the object with a bright field illuminating light and a dark field illuminating light portion comprising a plurality of segments, each of the plurality of segments configured to illuminate the object with a dark field illuminating light having uniform angular distribution over an effective field of view, the dark field illuminating light portion and the bright field illuminating light portion being disposed in the same light source plane; and
 an optical imaging system comprising an imaging sensor and configured to create a dark field image of the object,
the method comprising:
 a. selecting one of the plurality of segments based on the features of the object; and
 b. selecting a separate dark field image of the object, when the object is separately illuminated only by the selected one of the plurality of segments to achieve a predetermined direction of incidence of the dark field illuminating light;
wherein the optical imaging system is a telecentric optical imaging system further comprising a lower imaging module having a first optical axis and an upper imaging module having a second optical axis, wherein the illumination optical axis, the first optical axis, and the second optical axis are all parallel and are offset with respect to one another in a lateral direction, substantially perpendicular to the illumination optical axis, the first optical axis, and the second optical axis, and wherein light reflected by the object passes through both the lower imaging module and the upper imaging module prior to being incident on the imaging sensor.

* * * * *